United States Patent [19]
Guhle et al.

[11] Patent Number: 5,323,790
[45] Date of Patent: Jun. 28, 1994

[54] METHOD AND APPARATUS FOR TREATMENT OF UTERINE PROLAPSES IN LIVESTOCK

[76] Inventors: Arnold Guhle; Giraud Guhle, both of Box 403, Daysland, Alberta, Canada, T0B 1A0

[21] Appl. No.: 994,702

[22] Filed: Dec. 22, 1992

[30] Foreign Application Priority Data

Jan. 2, 1992 [CA] Canada .................. 2058697

[51] Int. Cl.$^5$ ...................... A61B 17/42; A61M 29/02
[52] U.S. Cl. ...................................... 128/898; 606/193
[58] Field of Search ................ 606/119, 193; 119/101, 119/143; 128/898

[56] References Cited

U.S. PATENT DOCUMENTS

| | | | |
|---|---|---|---|
| 1,584,464 | 5/9126 | Maranville | 606/119 |
| 2,825,330 | 3/1958 | Storz | 119/143 |
| 3,081,773 | 3/1963 | Isaac | 606/119 |
| 3,516,406 | 6/1970 | Jensen | 606/119 |

Primary Examiner—Tamara L. Graysay
Attorney, Agent, or Firm—Davis, Bujold & Streck

[57] ABSTRACT

A method of and apparatus for treating uterine prolapses in livestock. Firstly, clean and manually reposition the uterine prolapse. Secondly, insert an internal uterine support through a cervix and deep into a uterus of an animal thereby supporting the positioning of the uterus. Thirdly, block the removal of the internal uterine support for sufficient time to permit the cervix of the animal to contract. Fourthly, withdraw the internal uterine support once the cervix of the animal has contracted. The apparatus has an inflatable supporting member serving as the internal uterine support. The supporting member is positioned on an elongate member which is insertable through a cervix and into a uterus of the animal. When expanded the supporting member is of a size sufficient to provide internal uterine support and when contracted the supporting member can be withdrawn through the contracted cervix without causing discomfort to the animal.

1 Claim, 1 Drawing Sheet

METHOD AND APPARATUS FOR TREATMENT OF UTERINE PROLAPSES IN LIVESTOCK

The present invention relates to a method and apparatus for treatment of uterine prolapses in livestock.

BACKGROUND OF THE INVENTION

It is not uncommon for a cow or a sheep to push her uterus out of the birth canal when calving. When this occurs it is referred to as an "uterine prolapse". The method of treatment is for a veterinarian to manually reposition the uterus, and then place pins through the vulva to create an obstruction which prevents the uterus from being pushed out again. This treatment is effective only if the animal stops "pushing". In most cases, however, the uterus is pushed against the pins, the cervix does not contract to its normal size and the animal continues to push. The result is a painful condition that obstructs the normal bodily functions of the animal, leading to a gradual deterioration in the health of the animal and eventually death. Even if the treatment is effective, the piercing of the skin with pins can lead to a secondary problem of infection.

SUMMARY OF THE INVENTION

What is required is a more effective method and apparatus for treating uterine prolapses in livestock.

According to one aspect of the present invention there is provided a method of treating uterine prolapses in livestock which is comprised of the following described steps. Firstly, clean and manually reposition the uterine prolapse. Secondly, insert an internal uterine support through a cervix and deep into a uterus of an animal thereby supporting the positioning of the uterus. Thirdly, block the removal of the internal uterine support for sufficient time to permit the cervix of the animal to contract. Fourthly, withdraw the internal uterine support once the cervix of the animal has contracted.

The described method proved effective in treating the uterine prolapse condition, however, difficulty was encountered in withdrawing the internal uterine support once the cervix had contracted. The difficulties in withdrawing the internal uterine support necessitated that a special apparatus be developed.

According to another aspect of the invention there is provided an apparatus for treating uterine prolapses in livestock which is comprised of an elongate member having a first end and a second end. The elongate member is insertable through a cervix and into a uterus of an animal such that the first end is positioned substantially into the uterus and the second end extends out of the cervix. The elongate member is narrow such that the elongate member can be withdrawn from the uterus, after the cervix has contracted, without causing discomfort to the animal. A supporting member is positioned at the first end of the elongate member. The supporting member is expandable and contractible. When expanded the supporting member is of a size sufficient to provide internal uterine support and when contracted the supporting member can be withdrawn through the contracted cervix without causing discomfort to the animal. Means is provided at the second end of the elongate member for expanding and contracting the supporting member. Attachment means are provided at the second end of the elongate member whereby the elongate member is attachable to a positioning harness on the animal.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
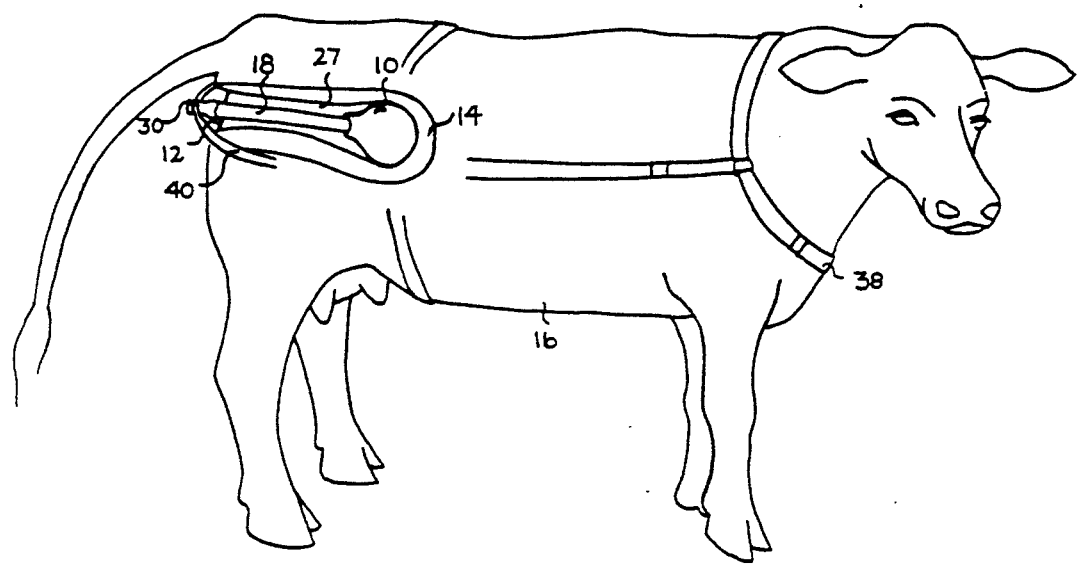
FIG. 1 is a diagrammatic side elevation view of a cow being treated in accordance with the teaching of the present method.

The preferred method of treating uterine prolapses in livestock will now be described with respect to FIG. 1. The method of treating uterine prolapses in cattle consists of the following described steps. Firstly, clean and manually reposition the uterine prolapse. It is preferred that this cleaning be done with a disinfectant, such as an iodine solution. Secondly, referring to FIG. 1, insert an internal uterine support, such as apparatus 10, through a cervix 12 and deep into a uterus 14 of a cow 16 thereby supporting the positioning of uterus 14. Thirdly, block the removal of the internal uterine support for sufficient time to permit the cervix of the animal to contract. Fourthly, withdraw apparatus 10 once cervix 12 of cow 16 has contracted. Cervix 12 will usually contract within in a period of three or four days.

Figure 2:
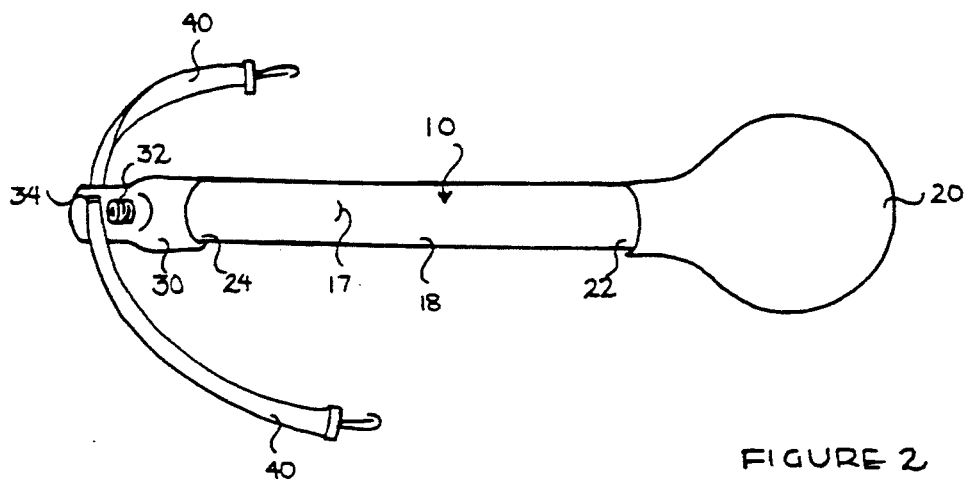
FIG. 2 is a side elevation view of an apparatus constructed in accordance with the teachings of the present invention.

The preferred embodiment, an apparatus for treating uterine prolapses in livestock generally identified by reference numeral 10, will now be described with reference to FIGS. 1 and 2. Referring to FIG. 2, apparatus 10 consists of an elongate tubular member 18 and an inflatable supporting member 20. Elongate member 18 has a first end 22, a second end 24 and a central passage 17 extending between first end 22 and second end 24. When elongate member is inserted through cervix 12 and into uterus 14 of cow 16 as illustrated in FIG. 1, first end 22 is positioned substantially into uterus 14 and second end 24 extends out of cervix 12. The preferred length of elongate member 18 is approximately 20 inches. Elongate member 18 is narrow to facilitate ease of withdrawal from uterus 14, after cervix 12 has contracted, without causing discomfort to the cow. The preferred thickness is 1 inch. Inflatable supporting member 20 is positioned at first end 22 of elongate member 18. Second end 24 of elongate member 18 is closed by an end cap 30. Supporting member 20 is expandable and contractible through the ingress and egress of air through a valve 32 on end cap 30. When expanded supporting member 20 is of a size sufficient to provide internal uterine support, as illustrated in FIG. 1, and when contracted supporting member 20 can be withdrawn through contracted cervix 12 without causing discomfort to the animal. The size to which inflatable supporting member 20 should be expanded varies with the size of the animal. Usually the size of a fist is sufficient. Elongate member 18 is inserted through cervix 12 at a time when cervix 12 is fully dilated. Inflatable supporting member 20 can, therefore, be inserted in an inflated condition. It is preferred that apparatus 10 be covered with a disposable plastic bag 27 in order to avoid spreading infection. This bag is disposed of after each use. Second end 24 of elongate member 18 has a slot 34 whereby elongate member 18 is attachable to a positioning harness 38 on cow 16. This attachment is accomplished by extending a strap 40 through slot 34 and fastening strap 40 to harness 38.

Once apparatus 10 is in place cow 16 can be released. It has been found that cow 16 stops pushing and experiences no further discomfort. Cow 16 resumes normal eating and will nurse her calf. The release of urine is not prevented by apparatus 10. After 3 days cervix 12 will have contracted and elongate member 18 can be removed from uterus 14. To effect the removal of apparatus 10, air is allowed to flow through valve 32 deflating inflatable supporting member 20. Elongate member 18 can then be drawn from contracted cervix 12 without causing cow 16 any discomfort.

It will be apparent to one skilled in the art that the described method is to be preferred over the pinning of the vulva. There is no puncturing of any kind, and therefore there is reduced likelihood of infection or pain to animal. It will also be apparent to one skilled in the art that modifications can be made to apparatus 10 without departing from the spirit and scope of the invention as defined in the claims.

The embodiments of the invention in which an exclusive property or privilege is claimed are defined as follows:

1. A method of treating uterine prolapses in livestock, comprising the steps of:
   a. firstly, cleaning and manually repositioning the uterine prolapse;
   b. secondly, inserting an expandable internal uterine support through a cervix and deep into a uterus of an animal thereby supporting the positioning of the uterus, the expandable internal uterine support being sized for withdrawal through the cervix of the animal after the cervix has contracted;
   c. thirdly, blocking the removal of the internal uterine support for sufficient time to permit the cervix of the animal to contract; and
   d. fourthly, contracting and withdrawing the internal uterine support once the cervix of the animal has been contracted.

* * * * *